United States Patent [19]

Cortes et al.

[11] Patent Number: 4,793,920
[45] Date of Patent: Dec. 27, 1988

[54] CHROMATOGRAPHY COLUMNS WITH CAST POROUS PLUGS AND METHODS OF FABRICATING SAME

[75] Inventors: Hernan Cortes; Curtis D. Pfeiffer; Bruce E. Richter; Timothy S. Stevens, all of Midland, Mich.

[73] Assignee: Lee Scientific, Inc., Salt Lake City, Utah

[21] Appl. No.: 111,147

[22] Filed: Oct. 20, 1987

Related U.S. Application Data

[63] Continuation of Ser. No. 807,729, Dec. 11, 1985, abandoned.

[51] Int. Cl.⁴ ............................................. B01D 15/08
[52] U.S. Cl. .............................. 210/198.2; 210/510.1; 55/386
[58] Field of Search ................... 210/656, 198.2, 510.1, 210/927; 65/18.1; 55/67, 197, 386

[56] References Cited

U.S. PATENT DOCUMENTS

| | | | |
|---|---|---|---|
| 2,136,170 | 11/1938 | Luertzing | 65/18.1 |
| 2,576,610 | 11/1951 | Kunzog | 210/510.1 |
| 2,723,756 | 11/1955 | Miller et al. | 210/198.2 |
| 3,440,864 | 4/1969 | Blume | 210/198.2 |
| 3,511,377 | 5/1970 | Hrdina | 210/198 |
| 3,533,767 | 10/1970 | Grant | 65/18.1 |
| 3,677,410 | 7/1972 | Okumura | 210/198.2 |
| 3,771,659 | 11/1973 | Fraser | 210/198.2 |
| 3,790,475 | 2/1974 | Eaton | 210/31 C |
| 4,088,449 | 5/1978 | Smith | 210/205 |
| 4,112,032 | 9/1978 | Blaszyk et al. | 264/42 |
| 4,131,542 | 12/1978 | Bergna | 210/656 |
| 4,142,858 | 3/1979 | Acuff | 210/656 |
| 4,157,299 | 6/1979 | Landowne | 210/658 |
| 4,181,853 | 1/1980 | Abu-Shumays et al. | 250/304 |
| 4,399,032 | 8/1983 | Mott | 210/198.2 |
| 4,415,631 | 11/1983 | Schutijser | 210/656 |
| 4,416,675 | 11/1983 | Montierth | 210/510.1 |
| 4,457,846 | 7/1984 | Munk | 210/198.2 |
| 4,469,628 | 9/1984 | Simmon | 210/688 |
| 4,483,773 | 11/1984 | Yang | 210/198.2 |

FOREIGN PATENT DOCUMENTS 7117173  7/1972  Netherlands ............... 210/198.2

*Primary Examiner*—Ernest G. Therkorn
*Attorney, Agent, or Firm*—Thorpe, North & Western

[57] ABSTRACT

Porous ceramic plugs are cast in place in chromatographic columns in order to provide supports for chromatographic beds in liquid chromatography devices and restrictors in supercritical fluid chromatographic devices. The supports are cast in place by fusing a silicate containing solution, such as one containing potassium silicate, which has been drawn into the outlet end of the column.

42 Claims, 1 Drawing Sheet

CHROMATOGRAPHY COLUMNS WITH CAST POROUS PLUGS AND METHODS OF FABRICATING SAME

This application is a continuation of application Ser. No. 807,729, filed Dec. 11, 1985, now abandoned.

BACKGROUND OF THE INVENTION

1. Field of the Invention

The instant invention relates to chromatography columns and methods of fabricating chromatography columns. More particularly, the instant invention relates to bed supports and restrictors for chromatography columns and to methods of fabricating such.

2. Technical Consideration and Prior Art

The trend in chromatography has been to move to higher pressures and smaller diameter columns for efficient solvent utilization and high column efficiency in high-performance liquid chromatography and for high column efficiency in supercritical fluid chromatography. By utilizing long chromatography columns or tubes, greater resolving power can be realized, allowing complex mixtures to be effectively separated.

Utilization of chromatography tubes having relatively small inner diameters in the range of preferrably 10–1000 $\mu$m are utilized to accomplish state-of-the-art chromatography. By having small inner diameters, generally not greater than about 2000 $\mu$m the volume defined by a chromatrography column is minimized. Accordingly, minute samples can be analyzed with state-of-the-art chromatrography columns. In order to increase the resolution of the sample components dissolved to a solvent within a chromatorgraphy column, the lengths of state-of-the-art columns are many orders of magnitude greater than the diameters thereof. For example, a chromatography column utilizing a liquid solvent might have a diameter of 250 $\mu$m and a length of approximately 1 meter, whereas a chromatography column utilized with supercritical fluid chromatography might have a length of 19 meters and a diameter of approximately 80 $\mu$m.

Generally, a chromatography column is packed with a sorbent which forms a chromatography bed. For example, the sorbent may be composed of microparticles such as $C_{18}$ bonded phase particles having diameters in the range of 1–10 $\mu$m which are suspended in a slurry and injected under pressure into the bore of the column. During injection of the slurry and during operation of the column, one end of the column must be fitted with a plug which may be for example a porous plug, in order to retain the sorbent therein. According to current practices, this is accomplished by inserting a glass wool plug in the downstream end of the column in order to form a support for the bed of sorbent. This approach to plugging the outlet end of the column has not provded totally satisfactory in that it is very difficult to insert the glass wool plug in such a small opening. Moreover, since there is nothing binding the glass wool plug to the wall of the column, the plugs on occasion are ejected from the columns due to pressure created within the columns during use thereof. This problem is addressed in U.S. Pat. No. 4,483,773 issued Nov. 20, 1984 to Yang, wherein alternatives to glass wool plugs are disclosed. These alternatives include utilizing narrow-bore tubing, wire, particles of a diameter larger than the constituent particles of the sorbent, and inserting a narrow-bore plug into a sleeve attached to the outside of the column. The patent to Yang clearly states that there is difficulty with the glass wool plug concept and resorts to a host of alternatives-the relative merits of which the instant inventors have little familiarity. Since the solvent in which the sample under analysis is dissolved must pass through the plug, the configuration of the plug directly affects the efficiency of the column. In part, the efficiency of the column is determined by the speed at which the solvent moves through the column and the amount of solvent which is utilized for a particular test. Generally, glass wool plugs provide high efficiency. Consequently, a desirability of any alternative to glass wool plugs should have an efficiency which at least approaches that of glass wool plugs.

In columns used for supercritical fluid chromatography (SFC) a restrictor is placed at the exit end of the chromatographic column. According to current practice, the restrictor is configured from a small-diameter capillary tube. Generally, the capillary tube forming the restrictor is butted or placed end-to-end against the chromatographic column and held in place by a union fitting or "butt-connector." Capillary tubing of Pyrex glass, fused silica and platinum iridium have been used as restrictors. The small-diameter capillary tube allows slow decompression of the mobile phase, or solvent, before detection. However, with this approach, relatively involatile solute molecules associate and condense along the walls of the small-diameter capillary tube. This results in both clogging of the opening and spiked peaks seen by the detector. In addition, laser-drilled orifices have been used as restrictors, but they are prone to blockage and breakage. Generally, these prior art restrictor designs are not entirely satisfactory in that they are separate from the columns and must be butted therewith or otherwise held in engagement therewith.

The prior art includes a number of teachings of porous plugs used with chromatography columns. For example, U.S. Pat. No. 3,440,864 discloses utilizing a porous stainless steel or fiberglass disc inserted into a chromatography column. U.S. Pat. No. 3,771,659 discloses a porous plug of any naturally porous or artificially porous material, such as Teflon, which is used with a chromatography column. U.S. Pat. No. 4,142,856 discloses a disc of microporous material formed from a polymer such as high-density polyethylene, which disc is inserted into a column. U.S. Pat. No. 4,181,853 utilizes a porous plug of sintered steel frit which is used in a chromatography system. U.S. Pat. No. 4,399,032 discloses a sintered metal terminator element having an outer rim which supposedly provides a seal with an outlet union retaining it. Each of these patents disclose arrangements of relative structural complexity wherein the plugs do not have the advantage of being unitary with the chromatographic column so that they effecitively seal with the walls of the column.

U.S. Pat. No. 2,723,756 discloses a cast-in-place plug made of plaster of Paris which is inserted in a large-diameter support cylinder. However, the plug is not actually in a chromatographic tube since the chromatographic column of this invention does not include a tube.

SUMMARY OF THE INVENTION

In view of the aforementioned considerations, it is an object of the instant invention to provide a new and improved plug for chromatographic columns which can be used as a sorbent bed support or as a restrictor. It is a further object of the instant invention to provide new and improved processes for forming such plugs.

Upon further study of the specification and appended claims, further objects and advantages of this invention will become apparent to those skilled in the art.

In view of the aforementioned objects, the instant invention contemplates a chromatographic column which includes a tube having a sorbent bed, an inner wall, and an inlet end and an outlet end, wherein the sorbent bed is retained within the tube by a bed support comprising a cast-in-place, ceramic plug disposed in the outlet end of the tube.

The instant invention further contemplates in a chromatographic column used for supercritical fluid chromatography, a tube containing a sorbent bed or a stationary phase coated or bonded to the inner wall, and having an inner wall and an inlet end and outlet wherein the outlet end includes a restrictor which is configured as a cast-in-place microporous ceramic plug, disposed within the outlet end and adhered to the inner wall of the tube.

The instant invention still further contemplates a process for fabricating a chromatographic column, wherein the column includes a tube of a selected material, the tube having an open end and an inner wall, wherein a microporous ceramic plug is formed in the open end by depositing a quantity of fusible material in the open end of the tube. A plug is then formed in situ at the end of the tube by causing the material to chemically fuse so that the material adheres to the inner wall of the tube to form a solid microporous mass. A sorbent is then packed into the tube upstream of the plug.

In accordance with a preferred embodiment of the invention, the afore-described process is accomplished by preparing a soluble silicate solution and separating the gels therefrom. The solution is then deposited within the open end of the tube and the open end of the tube heated to chemically fuse the solution and thereby form a plug of porous ceramic material which is integral with the open end of the tube.

BRIEF DESCRIPTION OF THE DRAWINGS

Various other objects, features and attendant advantages of the present invention will become more fully appreciated as the same becomes better understood when considered in conjunction with the accompanying drawings, in which like reference characteris designate the same or similar parts throughout the several views, and wherein.

DESCRIPTION OF THE PREFERRED EMBODIMENTS

Figure 1:
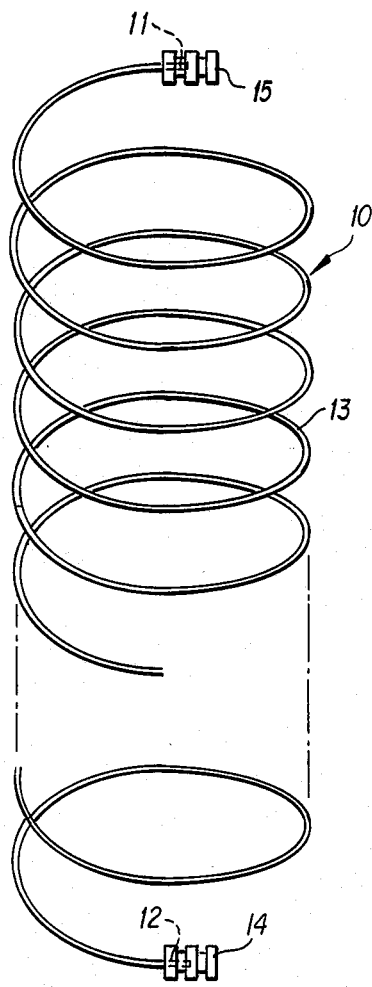
FIG. 1 is a perspective view of a chromatographic column which utilizes the principles of the instant invention.

Referring now to FIG. 1, there is shown a chromatographic column, designated generally by the numeral 10, which has an inlet end 11, an outlet end 12, and an intermediate portion 13 which contains a sorbent or coating on the inner wall for performing chromatographic analysis. Attached to the inlet end 11 of the chromatographic column 10 is a diagrammatically illustrated connector 15 which connects the column to the apparatus which introduces or injects the material to be analyzed, which material is dissolved or dispersed in a solvent. Connected to the outlet end 12 of the column 10 is a connector 14 for connecting the column to analytical equipment. In operation, the solvent is applied under pressure through the connector 15 so as to traverse the column 10 and exit through the outlet end 12 and the connector 14.

The column 10 is conveniently configured as a spiral because its length is usually several orders of magnitude greater than its diameter (specifically, its inner diameter). For example, if the column 10 is used for liquid chromatography, the inner diameter may be on the order of 250 $\mu$m, while the length of the column may be, for example, approximately 100 cm. On the other hand, if the chromatographical column 10 is used for supercritical fluid chromatography, the length of the column may be approximately 20 meters, while the inner diameter may be approximately 80 $\mu$m. In general, for liquid chromatography inner diameters in the range of about 10 to about 1000 $\mu$m are utilized, whereas in superciritical fluid chromatorgraphy, internal diameters in the range of about 10 to about 250 $\mu$m are utilized. In accordance with preferred practice, the chromatographic column 10 is fabricated of fused silica material in accordance with wellknown procedures and methods and has a very smooth inner wall surface.

Figure 2:
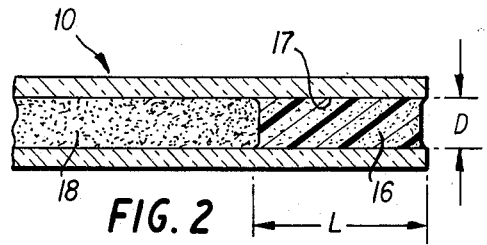
FIG. 2 is an enlarged cross-sectional view of the outlet end of the column of FIG. 1 showing a microporous ceramic plug disposed in the outlet end and adhered to the inner wall of the column forming the tube.

Referring now to FIGS. 1 and 2, the outlet end 12 of tube 10 is shown greatly enlarged. Within the outlet end 12 of the tube 10, a porous ceramic plug 16 of fused material is disposed. The plug 16 is adhered to the smooth inner wall surface 17 of the tube 10 and extends back from the outlet end 11 of the tube a distance "L" which varies in accordance with the purpose for which the plug is used. For example, if the plug 16 is used in a tube 10 that is part of a supercritical fluid chromatography system, the distance "L" might be 0.5 mm to 2 cm. If the plug 16 is being used for a liquid chromatography system, the distance "L" might be 0.5–3.0 mm. The selection of the distance "L" is also dependent on the particular inner diameter of the tube "D".

Disposed behind the porous ceramic plug 16 is a sorbent bed 18, which is normally injected into the tube 10 or a liquid stationary phase coated or bonded to the inner wall subsequent to forming the plug. Since the plug is porous, a suspension of sorbent 18 can be easily injected into the tube 10.

Figure 3A:
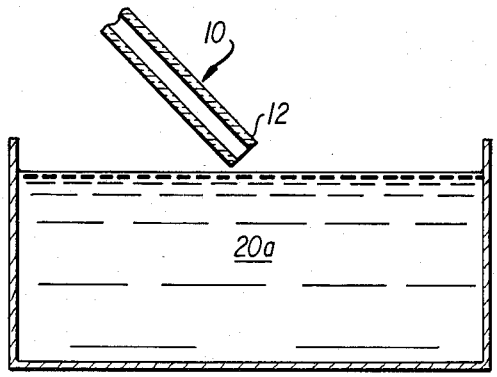
FIGS. 3a, 3b, 3c and 3d show the steps of fabricating the end plug shown in FIG. 2 wherein the outlet end of the column in immersed into a solution of fusible material, the fusible material is fused by the application of heat and a sorbent is thereafter injected into the tube.
Figure 3B:
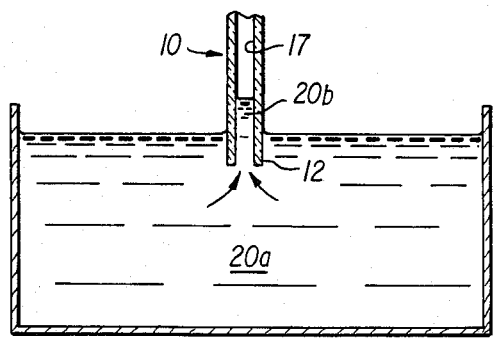
Figure 3C:
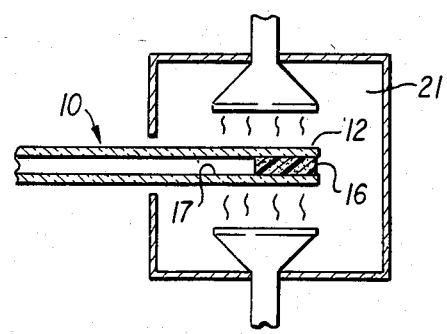
Figure 3D:
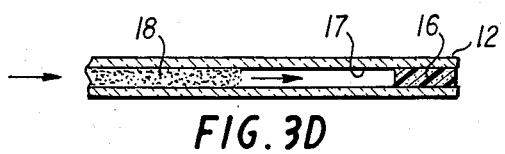
Figure 4:
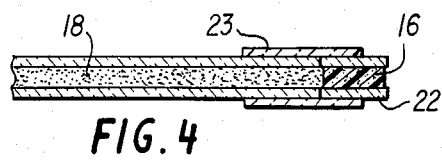
FIG. 4 is an enlarged cross-sectional view of another embodiment of the invention, wherein a microporous ceramic plug is formed in a section of capillary tube which is then abutted to the end of the chromatographic column.

Referring now to FIGS. 3a–3d, there is shown a preferred method for forming the plug 16. A solution 20a containing, for example potassium silicate, such as that known as Kasil Number 1, is provided. The solution is centrifuged to remove gels and the end 12 of the chromatographic column 10 is simply immersed therein as shown in FIG. 3b. A portion 20b of the solution is drawn up into the tube 10 by capillary action or introduced with, for example, a syringe. As shown in FIG. 3c, the end 12 of the chemically tube 10 with the fusible solution 20b is then heated by conventional means, such as a steambath 21, in order to fuse the solution 20b into the solid porous ceramic plug 16, while chemically adhering the material of the plug 16 of the inner wall 17 of the tube 10. Thereafter, the sorbent bed material 18 is packed into the tube 10.

The plug 16 may be used for two different purposes. If the chromatographic column 10 is being used for liquid chromatography, then the plug 16 serves as a support for the sorbent bed 18 so as to retain the sorbent bed 18 in the column both during packing of the sorbent bed into the column and during use of the column. The plug 16 withstands pressures applied to the inlet 11 end of the column 10 in excess of 8,000 psi while having a chromatrographic efficiency similar to the chromatographic efficiency of the glass wool plugs of the prior art.

The plug 16 may also be used as a restrictor in the outlet end of a chromatography tube 10 used for supercritical fluid chromatography. In this embodiment of the invention, it has been found that a plug 16 used as a restrictor minimizes the distance over which decompression of the supercritical fluid solvent occurs while increasing drastically the number of paths through the restrictor that the solvent may travel. Accordingly, molecular association and condensation is minimized and at best totally eliminated. Consequently, line clogging is avoided as well as detector "spiking". In addition, the plug 16 does not cause band spreading. The cast in situ, or cast-in-place, porous ceramic plug 16 is of special interest in reducing spiking which occurs with higher molecular weight samples and in reducing the exit clogging which also occurs with high molecular weight samples. While a restrictor 16 is shown in FIG. 2 which is cast in place directly to the chromatographic tube 10, the restrictor may be formed on a separate portion of silica capillary tube 22 and the separate portion coupled to the outlet end 12 of the chromatographic tube 10 with a coupling 23.

While the plug 16 shown in the drawings and discussed thus far herein extends completely across the cross-section of the outlet end 12 of the tube 10, it is within the scope of this invention to interrupt this extension by incorporating fibers, hollow tubes and the like within the plug.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A support bed or support structure for supporting sorbent within a fused silica liquid chromatographic column having an internal diameter of 250 $\mu$m and a length of 99 cm was prepared by immersing the outlet end of the column in a solution of potassium silicate, removing the outlet end from the potassium silicate and heating the outlet end in a steam bath for approximately one hour to cause polymerization of the potassium silicate solution. The potassium silicate solution was a solution of Kasil Number 1 having a weight ratio of silicon dioxide to water of 2.50 and a density of 29.80 be' to which formamide was added in a ratio of 85% Kasel Number 1 to 15% formamide. Before immersing the outlet end of the chromatographic column in the solution, the solution was centrifuged to precipitate gels.

After the porous ceramic plug, according to the instant invention, was formed in the outlet end of the chromatographic tube in order to form a support for the sorbent, a pressure of 8,000 psi was supplied to the inlet end of the column in order to test the integrity of the plug and the adherence of the plug material to the very smooth interior surface of the chromatographic tube.

The chromatographic tube was then packed with ZORBAX® ODS, 7 $\mu$m particle size (DuPont, Wilmington, Del. U.S.A.) and tested. In the initial test, the length of the plug forming the support was approximately 4 cm. The resulting chromatogram indicated very poor efficiency, much lower than that obtained by using the prior art glass wool approach.

EXAMPLE 2

All of the steps of Example 1 were repeated with the exception of reducing the length of the plug to 1 mm. Upon filling the chromatographic tube with sorbent and testing the tube, very good results were attained with efficiencies comparable to using a good wool plug, but without the drawbacks of using glass wool plugs.

EXAMPLE 3

A chromatographic column used in supercritical fluid chromatography was provided with a porous ceramic plug for use as a restrictor in the outlet end of the column. As with Examples 1 and 2, a solution Kasil Number 1 and formamide was prepared in a ratio of 85% Kasil Number 1 to 15% formamide. The solution was centrifuged to precipitate the gels. A portion of fused silica capillary material having a length of about 2 cm and an internal diameter of 80 $\mu$m was immersed into the solution and a plug cast therein by heating the capillary material for about 1 hour in a steam bath. The capillary material was then connected to the end of an analytical chromatographic column having an internal diameter of 80 $\mu$m a length of 19 meters and a film of polysiloxane stationary phase 0.25 $\mu$m thick. The column was tested by running high molecular weight hydrocarbons (paraffin wax) therethrough. In the resulting test, no spiking occurred and there was no band spreading attributable to the fused, microporous plug. Moreover, there was no clogging. The length of the microporous plug in this particular example was about 2 cm long. The sample analyzed was a mixture of $C_{14}$, $C_{18}$, $C_{20}$, $C_{22}$, $C_{24}$ and $C_{26}$ n-alkanes.

The preceding examples can be repeated with similar success by substituting the generically or specifically described reactancts and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for fabricating a chromatographic column wherein the column includes a capillary tube of a selected material, the tube having an open end and an inner wall having a silica component, the process comprising the steps of:

(a) providing a chemically fusible material which is microporous upon casting and which adheres to the specific material of the tube upon fusing, which chemically fusible material comprises a composition having a silicate component;
(b) depositing a quantity of the chemically fusible material in the tube; and
(c) casting a plug in situ by fusing the material within the tube and chemically adhering the material to the inner wall of the tube to form a solid microporous mass having a length along the tube within the range of between less than 4 centimeters and more than 10 microns.

2. The process of claim 1, wherein the fusible material is a heat fusible material and wherein the step of casting the plug in situ includes heating the material.

3. The process of claim 1, wherein the solution further includes formamide mixed with the silicate.

4. The process of claim 3, wherein the silicate is potassium silicate.

5. The process of claim 1, wherein the step of depositing the fusible material in the tube comprises immersing the open end of the tube in the fusible material and allowing the material to be drawn into the tube.

6. The process of claim 1, wherein the chromatographic column is used for supercritical fluid chromatography and wherein the plug is disposed in the tube and the plug forms a microporous restrictor restricting flow within the tube.

7. The process of claim 6, wherein the tube has an inner diameter in the range of about 10 $\mu$m to about 500 $\mu$m.

8. The process of claim 7, wherein the tube has an inner diameter of about 80 $\mu$m.

9. The process of claim 1 wherein the tube has a coating on the inner wall of the tube which coating serves as a stationary phase.

10. The process of claim 1 wherein the step of casting a plug in situ comprises injecting the material into the tube such that a plug is formed at a location remote from the open end of the tube.

11. The process of claim 1 further comprising the step of filling the tube with a sorbent to form a chromatographic bed which bed is retained within the tube by the plug.

12. The process of claim 11, wherein said plug supports the sorbent which forms the chromatographic bed.

13. The process of claim 12, wherein the said plug is cast in the end of the tube which forms an outlet for the chromatographic column.

14. The process of claim 13, wherein the tube is a small diameter tube having an inner diameter in the range of about 10 $\mu$m to about 1000 $\mu$m.

15. The process of claim 14 wherein the tube has an inner diameter of about 250 $\mu$m.

16. The process of claim 11, wherein the filling step comprises packing the tube with a sorbent suspension.

17. The chromatographic column of claim 16, wherein the material of the plug extends uniformly across the tube.

18. In a chromatographic column used for supercritical fluid chromatography, a tube having a silica component and having an inner wall and containing a chromatographic bed or a liquid stationary phase coated or bonded to the inner wall, an inlet end and an outlet end, the outlet end including a restrictor, which restrictor allows controlled expansion of a supercritical fluid; the restrictor being configured as a plug of microporous ceramic material having a silica component and having a length along the tube within the range of between less than 4 centimeters and more than 10 micron and which has been cast in situ and which is chemically adhered to the inner wall of the tube, whereby: a multitude of paths are provided for solutes to exit from the column, the distance over which decompression occurs is controlled, and molecular association and condensation is minimized within the plug.

19. The chromatographic column of claim 18, wherein the tube has an inner diameter in the range of about 10 $\mu$m to about 500 $\mu$m.

20. The chromatographic column of claim 19, wherein the tube has an inner diameter of about 80 $\mu$m.

21. The chromatographic column of claim 20 wherein the restrictor has a length of between less than 4 centimeters and more than 10 microns.

22. In a chromatographic column, a tube having a silica component and containing a chromatographic bed and having an inner wall, inlet end and an outlet end, a bed support positioned at the outlet end for supporting the chromatographic bed; the bed support being a plug of porous ceramic material having a silica component and having a length along the tube within the range of between less than 4 centimeters and more than 10 microns which has been cast in situ at the outlet end and chemically adhered to the inner wall of the tube.

23. The chromatographic column of claim 22, wherein the inner diameter of the tube is in the range of about 10 $\mu$m to about 500 $\mu$m.

24. The chromatographic column of claim 23, wherein the inner diameter of the tube is approximately 250 $\mu$m and the length of the bed support is in the range of 0.50 mm to 3.0 mm.

25. The chromatographic column of claim 24 wherein the length of the tube is about 100 cm.

26. The chromatographic column of claim 22 wherein the material of the plug extends uniformly across the tube.

27. A chromatographic apparatus for retention of selected material within a tube comprising:
a tube having a silica component; and
a plug having a silica component and having a length along the tube within the range of between less than 4 centimeters and more than 10 microns and disposed within the interior of the tube, said plug being made of a fusible microporous material such that said selected materials can be retained within said tube, wherein said plug is chemically fused to the interior wall of said tube.

28. An apparatus for retention of selected material within a tube as defined in claim 27 wherein said chromatographic column is a gas chromatographic column.

29. An apparatus for retention of selected material within a tube as defined in claim 27 wherein said chromatographic column is a liquid chromatographic column.

30. An apparatus for retention of selected material with a tube as defined in claim 27 wherein said chromatographic column is a supercritical fluid chromatographic column.

31. An apparatus for retention of selected material within a tube as defined in claim 27 wherein said plug extends uninterrupted completely across the interior diameter of the tube.

32. An apparatus for retention of selected material within a tube as defined in claim 27 wherein the extension of said plug across the interior diameter of the tube is interrupted by at least one object disposed within the plug.

33. An apparatus for retention of selected material within a tube as defined in claim 27 wherein said fusible material is prepared from a soluble silicate solution.

34. An apparatus for retention of selected material within a tube as defined in claim 33 wherein said silicate solution is potassium silicate.

35. A chromatographic apparatus including means for controlling pressure change between the interior and exterior of a tube comprising:
   a tube having a silica component; and
   a plug having a silica component and having a length along the tube within the range of between less than 4 centimeters and more than 10 microns and disposed within the interior of the tube, said plug being made of a fusible microporous material such that a controlled pressure differential can be created between the interior and exterior of the tube, wherein said plug is chemically fused to the interior wall of said tube and wherein said plug is sized and dimensional so that it is capable of controlling pressure change between the interior and exterior of said tube.

36. An apparatus for controlling pressure change between the interior and exterior of a tube as defined in claim 35 wherein said chromatographic column is a gas chromatographic column.

37. An apparatus for controlling pressure change between the interior and exterior of a tube as defined in claim 35 wherein said chromatographic column is a liquid chromatographic column.

38. An apparatus for controlling pressure change between the interior and exterior of a tube as defined in claim 35 wherein said chromatographic column is supercritical fluid chromatographic column.

39. An apparatus for controlling pressure change between the interior and exterior of a tube as defined in claim 35 wherein said plug extends uninterrupted completely across the interior diameter of the tube.

40. An apparatus for controlling pressure change between the interior and exterior of a tube as defined in claim 35 wherein the extension of said plug across the interior diameter of the tube is interrupted by at least one object disposed within the plug.

41. An apparatus for controlling pressure change between the interior and exterior of a tube as defined in claim 35 wherein said fusible material is prepared from a soluble silicate solution.

42. An apparatus for for controlling pressure change between the interior and exterior of a tube as defined in claim 41 in which said silicate solution is potassium silicate.

* * * * *